(12) United States Patent
Burkhardt, III et al.

(10) Patent No.: US 8,574,844 B2
(45) Date of Patent: Nov. 5, 2013

(54) QUANTITATIVE REAL-TIME ASSAY FOR NOROVIRUSES AND ENTEROVIRUSES WITH BUILT IN QUALITY CONTROL STANDARD

(75) Inventors: William Burkhardt, III, Mobile, AL (US); Michael C. L. Vickery, Burmingham, AL (US); Jessica Nordstrom, Irvington, AL (US)

(73) Assignee: The United States of America as represented by the Department Secretary of Health and Human Services, Washington, DC (US)

( * ) Notice: Subject to any disclaimer, the term of this patent is extended or adjusted under 35 U.S.C. 154(b) by 1308 days.

(21) Appl. No.: 11/865,228

(22) Filed: Oct. 1, 2007

(65) Prior Publication Data
US 2012/0129151 A1   May 24, 2012

Related U.S. Application Data

(63) Continuation of application No. 10/994,158, filed on Nov. 19, 2004, now abandoned.

(51) Int. Cl.
*C12Q 1/68* (2006.01)
*C12P 19/34* (2006.01)
*C07H 21/04* (2006.01)

(52) U.S. Cl.
USPC ........ 435/6.12; 435/6.1; 435/6.11; 536/24.33

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 5,618,703 A | 4/1997 | Gelfand et al. | |
| 5,952,202 A | 9/1999 | Aoyagi et al. | |
| 6,699,703 B1 | 3/2004 | Doucette-Stamm et al. | |
| 2001/0000148 A1 | 4/2001 | Kurane et al. | |
| 2001/0000175 A1 | 4/2001 | Kurane et al. | |
| 2001/0007985 A1 | 7/2001 | Rothberg et al. | |
| 2001/0024784 A1 | 9/2001 | Wagner | |
| 2002/0058256 A1 | 5/2002 | Rothberg et al. | |
| 2002/0102548 A1 | 8/2002 | Zimmermann et al. | |
| 2002/0106653 A1 | 8/2002 | Kurane et al. | |
| 2002/0137039 A1 | 9/2002 | Gessner | |
| 2002/0164613 A1 | 11/2002 | Villarete et al. | |
| 2002/0168631 A1 | 11/2002 | Park et al. | |
| 2003/0017482 A1 | 1/2003 | Godfrey et al. | |
| 2003/0032049 A1 | 2/2003 | Wagner | |
| 2003/0044826 A1 | 3/2003 | Ward et al. | |
| 2003/0082582 A1 | 5/2003 | Gatti | |
| 2003/0082592 A1 | 5/2003 | Kurane et al. | |
| 2003/0211527 A1 | 11/2003 | Hartman et al. | |
| 2005/0048475 A1* | 3/2005 | Paul et al. | 435/5 |
| 2006/0166232 A1 | 7/2006 | Vickery et al. | |

FOREIGN PATENT DOCUMENTS

| | | |
|---|---|---|
| WO | WO 00/29613 | 5/2000 |
| WO | WO 01/46463 | 6/2001 |
| WO | WO 02/29119 | 4/2002 |
| WO | WO 02/29120 | 4/2002 |
| WO | WO 0229119 A1 * | 4/2002 |
| WO | WO 0229120 A1 * | 4/2002 |
| WO | WO 02/052030 | 7/2002 |
| WO | WO 2004/104229 | 12/2004 |
| WO | WO 2004104229 A2 * | 12/2004 |

OTHER PUBLICATIONS

Hohne et al., "Detection and characterization of norovirus outbreaks in Germany: Application of a one-tube RT-PCR using a fluorogenic real-time detection system," Journal of Medical Virology, Feb. 2004, vol. 72, No. 2, pp. 312-319 [available on-line Dec. 18, 2003].*
Doornum et al., "Diagnosing Herpesvirus Infections by Real-Time Amplification and Rapid Culture," Journal of Clinical Microbiology, Feb. 2003, vol. 41, No. 2, pp. 576-580.*
Ando et al., "Genetic Classification of 'Norwalk-like Viruses'", J. Infect. Dis., 181:S336-S348 (2000).
Berg et al., "Multi-State Outbreaks of Acute Gastroenteritis Traced to Fecal-Contaminated Oysters Harvested in Louisiana", J. Infect. Dis., 181:S381-S386 (2000).
Blackburn et al., Morb Mortal Wkly Rep, 53(SS-8):23-39 (2004).
Center for Disease Control and Prevention, Morb. Mortal. Wkly. Rep., 50(RR02):1-69 (2001).
Center for Disease Control and Prevention, Morb. Mortal. Wkly. Rep., 51(49):1112-1115 (2002).
International Search Report mailed Jan. 24, 2005.
Deneen et al., "The Impact of Foodborne Calicivirus Disease: The Minnesota Experience", J. Infect. Dis., 181:S281-S283 (2000).
Donaldson et al., "Detection, quantitation and identification of enteroviruses from surface waters and sponge tissue from the Florida Keys using real-time RT—PCR", Water Res., 36:2505-2514 (2002).
Gallimore et al., "Diversity of Noroviruses Cocirculating in the North of England from 1998 to 2001", J. Clin. Microbiol., 42: 1396-1401 (2004).
Hara-Kudo, Y. et al., "Improved Method for Detection of *Vibrio parahaemolyticus* in Seafood," Appl. Environ. Microbiol., vol. 67, No. 12, pp. 5819-5823 (Dec. 2001).

(Continued)

*Primary Examiner* — Young J Kim
(74) *Attorney, Agent, or Firm* — Sheridan Ross P.C.

(57) ABSTRACT

A method is provided for reverse transcription-polymerase chain reaction (RT-PCR) accomplished by: a) amplifying a reverse transcribed cDNA in a mixture containing Norovirus Genogroup I and Norovirus Genogroup II primers and probes, in which the Norovirus primers and probes can distinguish between Genogroup I and Genogroup II viruses; b) quantifying virus; and c) normalizing data based on a universal internal RNA control. Optionally, the method may also include primers and probes for Enteroviruses. The present invention also provides a reaction mixture containing Norovirus Genogroup I and Norovirus Genogroup II primers and probes, in which the Norovirus primers and probes can distinguish between Genogroup I and Genogroup II viruses and universal internal RNA control primers and probes.

32 Claims, 6 Drawing Sheets

(56) References Cited

OTHER PUBLICATIONS

Hartman, L. et al., "Development of a Novel Internal Positive Control for Taqman® Based Assays," ASM Abstract Database, 1 page (Copyright 2003).

Kageyama et al., "Broadly Reactive and Highly Sensitive Assay for Norwalk-Like Viruses Based on Real-Time Quantitative Reverse Transcription—PCR", J. Clin. Microbiol., 41:1548-1557 (2003).

Katayama et al., "Phylogenetic Analysis of the Complete Genome of 18 Norwalk-like Viruses", Virol., 299:225-239 (2002).

Ke, D. et al., "Development of Conventional and Real-Time PCR Assays for the Rapid Detection of Group B *Streptococci*," Clinical Chemistry, vol. 46, No. 3, pp. 324-331 (2000).

Kojima et al., "Genogroup-specific PCR primers for detection of Norwalk-like viruses", J. Virol. Methods, 100:107-114(2002).

Monpoeho, S. et al., "Application of a Real-Time Polymerase Chain Reaction with Internal Positive Control for Detection and Quantification of Enterovirus in Cerebrospinal Fluid," Eur. J. Clin. Microbiol. Infect. Dis., vol. 21, pp. 532-536 (2002).

Myers, M. et al., "PCR Detection of a Newly Emerged Pandemic *Vibrio parahaemolyticus* O3:K6 Pathogen in Pure Cultures and Seeded Waters from the Gulf of Mexico," Appl. Environ. Microbiol., vol. 69, No. 4, pp. 2194-2200 (Apr. 2003).

Richards et al., "A SYBR green, real-time RT—PCR method to detect and quantitate Norwalk virus in stools", J. Virol. Methods, 116: 63-70 (2004).

Rosenstraus, M. et al., "An Internal Control for Routine Diagnostic PCR: Design, Properties, and Effect on Clinical Performance," J. Clin. Microbiol., vol. 36, No. 1, pp. 191-197 (Jan. 1998).

Sequence Alignment cited in Office Action, U.S. Appl. No. 10/994,158, mailed Dec. 14, 2006.

Shieh et al., "Detection of Norwalk-like Virus in Shellfish Implicated in Illness", J. Infect. Dis., 181:S360-S366 (2000).

Stöcher, M. et al., "A convenient approach to the generation of multiple internal control DNA for a panel of real-time PCR assays," Journal of Virological Methods, vol. 108, pp. 1-8 (2003).

Stöcher, M. et al., "A simple approach to the generation of heterologous competitive internal controls for real-time PCR assays on the LightCycler," Journal of Clinical Virology, vol. 25, pp. S47-S53 (2002).

TaqMan® Exogenous Internal Positive Control Reagents VIC™ Probe Protocol, Applied Biosystems, pp. i-ii, 1-23 (Copyright 2001).

Vickery, M. et al., "Detection and Quantification of Total and Potentially Virulent *Vibrio parahaemolyticus* Using a 4-Channel Multiplex Real-Time PCR Targeting the tl, tdh, and trh Genes and a Novel PCR Internal Control," ASM 2003 Annual Meeting, Poster #Q-082, pp. 1-8 (2003).

Wang, A. et al., "Quantitation of mRNA by the polymerase chain reaction," Proc. Natl. Acad. Sci. USA, vol. 86, No. 24, pp. 9717-9721 (Dec. 1989).

Wellinghausen, N. et al., "Detection of Legionellae in Hospital Water Samples by Quantitative Real-Time LightCycler PCR," Appl. Environ. Microbiol., vol. 67, No. 9, pp. 3985-3993 (Sep. 2001).

Yan et al., "Detection of norovirus (GI, GII), Sapovirus and astrovirus in fecal samples using reverse transcription single-round multiplex PCR", Journal of Virological Methods, 114:37-44 (2003).

Yoder et al., Morb. Mortal. Wkly. Rep., 53(SS-8):1-15 (2004).

Zimmermann, K. et al., "Technical Aspects of Quantitative Competitive PCR," BioTechniques, vol. 21, No. 2, pp. 268-270, 272, 274-279 (1996).

\* cited by examiner

SEQUENCE LISTING

```
<160> NUMBER OF SEQ ID NOS: 14

<210> SEQ ID NO 1
<211> LENGTH: 20
<212> TYPE: DNA
<213> ORGANISM: Norovirus
<220> FEATURE:
<221> NAME/KEY: misc_feature
<222> LOCATION: (12)..(12)
<223> OTHER INFORMATION: n is a, c, t or g

<400> SEQUENCE: 1
cgytggatgc gnttycatga                                           20

<210> SEQ ID NO 2
<211> LENGTH: 22
<212> TYPE: DNA
<213> ORGANISM: Norovirus

<400> SEQUENCE: 2
cttagacgcc atcatcatty ac                                        22

<210> SEQ ID NO 3
<211> LENGTH: 20
<212> TYPE: DNA
<213> ORGANISM: Norovirus

<400> SEQUENCE: 3
agatygcgat cycctgtcca                                           20

<210> SEQ ID NO 4
<211> LENGTH: 20
<212> TYPE: DNA
<213> ORGANISM: Norovirus

<400> SEQUENCE: 4
agatcgcggt ctcctgtcca                                           20

<210> SEQ ID NO 5
<211> LENGTH: 26
<212> TYPE: DNA
<213> ORGANISM: Norovirus
<220> FEATURE:
<221> NAME/KEY: misc_feature
<222> LOCATION: (9)..(9)
<223> OTHER INFORMATION: n is a, c, t or g

<400> SEQUENCE: 5
```
cargarbcna tgttyagrtg gatgag                                         26

<210> SEQ ID NO 6
<211> LENGTH: 21
<212> TYPE: DNA
<213> ORGANISM: Norovirus

<400> SEQUENCE: 6
tcgacgccat cttcattcac a                                              21

<210> SEQ ID NO 7
<211> LENGTH: 20
<212> TYPE: DNA
<213> ORGANISM: Norovirus

<400> SEQUENCE: 7
tgggagggcg atcgcaatct                                                20

<210> SEQ ID NO 8
<211> LENGTH: 17
<212> TYPE: DNA
<213> ORGANISM: Enterovirus

<400> SEQUENCE: 8
cctccggccc ctgaatg                                                   17

<210> SEQ ID NO 9
<211> LENGTH: 19
<212> TYPE: DNA
<213> ORGANISM: Enterovirus

<400> SEQUENCE: 9
caccggatgg ccaatccaa                                                 19

<210> SEQ ID NO 10
<211> LENGTH: 25
<212> TYPE: DNA
<213> ORGANISM: Enterovirus

<400> SEQUENCE: 10
cggacaccca aagtagtcgg ttccg                                          25

<210> SEQ ID NO 11
<211> LENGTH: 19
<212> TYPE: DNA
<213> ORGANISM: Artificial Sequence
<220> FEATURE:
<223> OTHER INFORMATION: Universal Internal RNA PCR Primer IC-46F

<400> SEQUENCE: 11
gacatcgata tgggtgccg                                                 19

<210> SEQ ID NO 12
<211> LENGTH: 21
<212> TYPE: DNA
<213> ORGANISM: Artificial Sequence
<220> FEATURE:
<223> OTHER INFORMATION: Universal Internal RNA PCR Primer IC-194R -continued

```
<400> SEQUENCE: 12
aatattcgcg agacgatgca g                                          21

<210> SEQ ID NO 13
<211> LENGTH: 26
<212> TYPE: DNA
<213> ORGANISM: Artificial Sequence
<220> FEATURE:
<223> OTHER INFORMATION: Universal Internal RNA PCR Probe IC-P

<400> SEQUENCE: 13
tctcatgcgt ctccctggtg aatgtg                                     26

<210> SEQ ID NO 14
<211> LENGTH: 311
<212> TYPE: DNA
<213> ORGANISM: Artificial Sequence
<220> FEATURE:
<223> OTHER INFORMATION: Universal Internal Control Molecule

<400> SEQUENCE: 14
ttcatgtggt cacagccctg acgaagctgt catcaagttc ataatgacat cgatatgggt    60
gccgttcgag cagtttagcc ctaaatcacc ctaccggcag acgtatgtca cattcaccag   120
ggagacgcat gagattggat gctgttgtgc gccctcaaca atgtaacgaa tggctgcatc   180
gtctcgcgaa tattgtcgta ccatcatctg acttggctca tgtctgcaag aggcttcgca   240
ctgggcttta tgaagggcga attctgcaga tatccatcac actggcggcc gctcgagcat   300
gcatctagag g                                                       311
```

QUANTITATIVE REAL-TIME ASSAY FOR NOROVIRUSES AND ENTEROVIRUSES WITH BUILT IN QUALITY CONTROL STANDARD

CROSS REFERENCE TO RELATED APPLICATION

This application is a continuation of U.S. patent application Ser. No. 10/994,158, filed Nov. 19, 2004, the disclosure of which is incorporated herein by reference.

GOVERNMENTAL INTERESTS

This invention was developed employing support from the United States Food and Drug Administration. The Government of the United States of America may have certain rights in this invention.

FIELD OF THE INVENTION

This invention relates to methods and reagents for detecting and quantifying viruses including Norovirus or Enterovirus by, for example, detecting or quantifying nucleic acids.

BACKGROUND OF THE INVENTION

Noroviruses are estimated to be responsible for two-thirds of the non-bacterial food-borne illness and nearly all (96%) of the non-bacterial gastrointestinal illnesses each year in the United States. Norovirus infection occurs via the fecal-oral route from contaminated food such as oysters (Berg et al., 2000, *J. Infect. Dis.*, 181:S381-S386; Shieh et al., 2000, *J. Infect. Dis.*, 181: S360-S366), water (Yoder et al., 2004, *Morb. Mortal. Wkly. Rep.*, 53(SS-8): 1-15; Blackburn et al., 2004, *Morb Mortal Wkly Rep*, 53(SS-8): 23-39) and even bakery products (Deneen et al., 2000, *J. Infect. Dis.*, 181: S281-S283). Infections also occur by droplet transmission, contact with contaminated fomites, or person-to-person transmission in contained or semi-contained areas such as cruise ships (Center for Disease Control and Prevention, 2002, *Morb. Mortal. Wkly. Rep.*, 51(49): 1112-1115), hospitals, nursing homes, restaurants, and schools (Gallimore et al., 2004, *J. Clin. Microbiol.*, 42: 1396-1401).

Noroviruses can not be propagated by cell culture techniques. However, Noroviruses are now detectable by various Reverse Transcription Polymerase Chain Reaction (RT-PCR) techniques. Real-time RT-PCR assays have been developed using either SYBR® Green and TaqMan® style assays for the detection and subsequent quantification of these viruses (Donaldson et al., 2002, *Water Res.*, 36: 2505-2514; Kageyama et al., 2003, *J. Clin. Microbiol.*, 41: 1548-1557; Kojima et al., 2002, *J. Virol. Methods*, 100: 107-114; Richards et al., 2004, *J. Virol. Methods*, 116: 63-70). SYBR® green assays, while useful for detection, are not reliable in quantification of template concentration due to its non-specific intercalation into any double stranded DNA (primer-dimer and products of non-specific amplification). There remains a need for methods and reagents that can detect or quantify more than one type of Norovirus and/or Enterovirus in a reaction mixture.

SUMMARY OF THE INVENTION

The present invention includes methods and reagents for detecting and quantifying viruses including Norovirus and Enterovirus by, for example, detecting or quantifying nucleic acids. The methods can employ and the reagents can include primers and oligonucleotide probes configured for a multiplex, real-time quantitative RT-PCR (qRT-PCR) assay. The present method can employ a universal internal RNA control. This internal control nucleic acid molecule can provide more efficient RT-PCR, allow normalization of results, and/or can detect inhibitors of RT-PCR.

In an embodiment, the present method can detect and quantify Norovirus Genogroup I and Norovirus Genogroup II in a single reaction. Detection and quantification of the two viruses from the two genogroups can be simultaneous. The reaction mixture can include an universal internal RNA control. The method can employ primers and oligonucleotide probes that distinguish between Norovirus Genogroups I and II. Optionally, the method of invention can employ primers and oligonucleotide probes that hybridize to Enterovirus nucleic acid.

In an embodiment, the present invention includes a reaction mixture including Norovirus Genogroup I and Norovirus Genogroup II primers and oligonucleotide probes, an internal control nucleic acid molecule, and internal RNA control primers and oligonucleotide probe. Said Norovirus primers are capable of distinguishing Genogroup I and Genogroup II. Optionally, a reaction mixture can also include primers and oligonucleotide probes for Enterovirus nucleic acids. An embodiment includes Norovirus Genogroups I and II primers and probes, an internal control nucleic acid molecule, and internal control primers and probes packaged together in a kit.

DETAILED DESCRIPTION

Definitions

Figure 1:
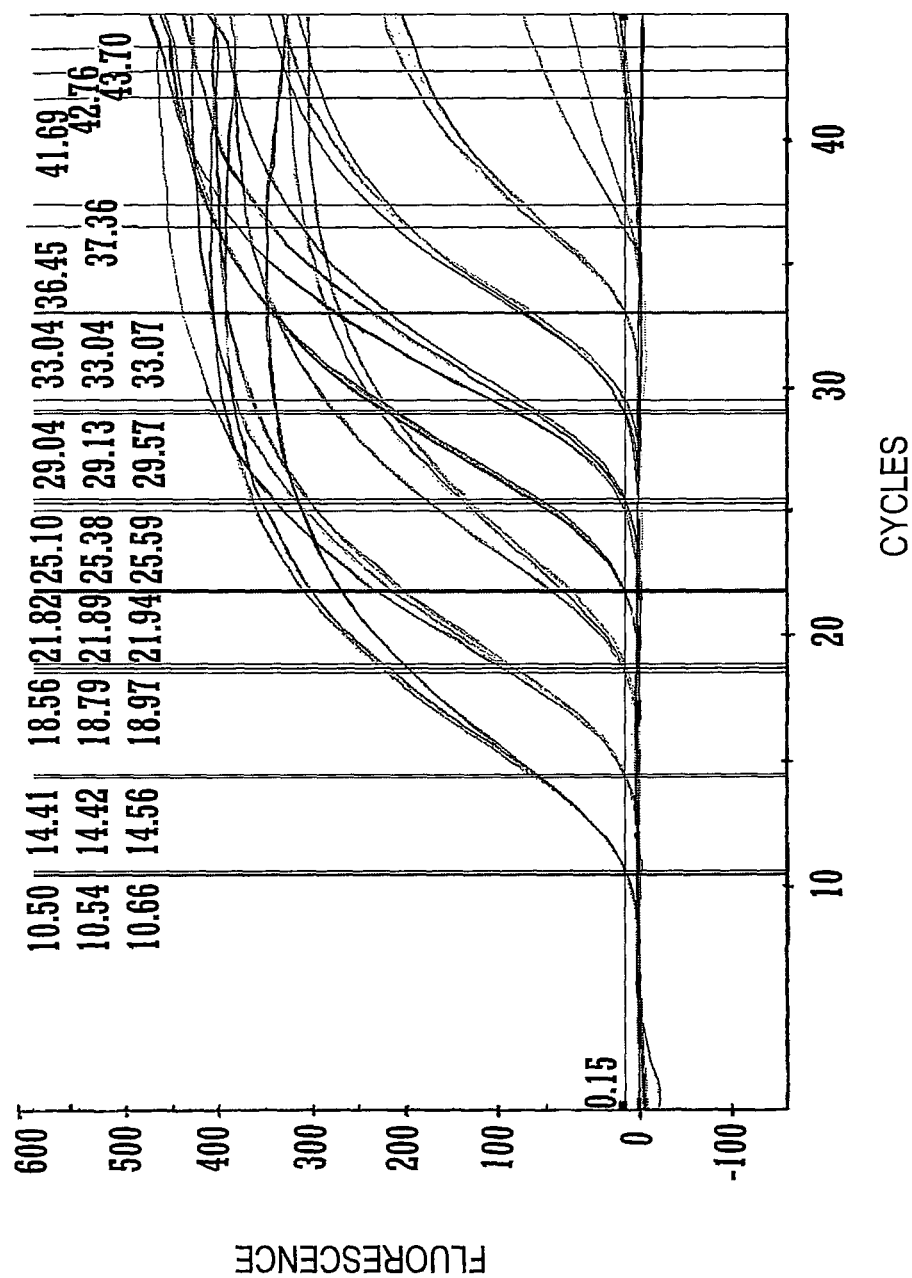
FIG. 1 is the standard curve established for the quantification of Norovirus Genogroup I using FAM-labeled oligonucleotide probes.
Figure 2:
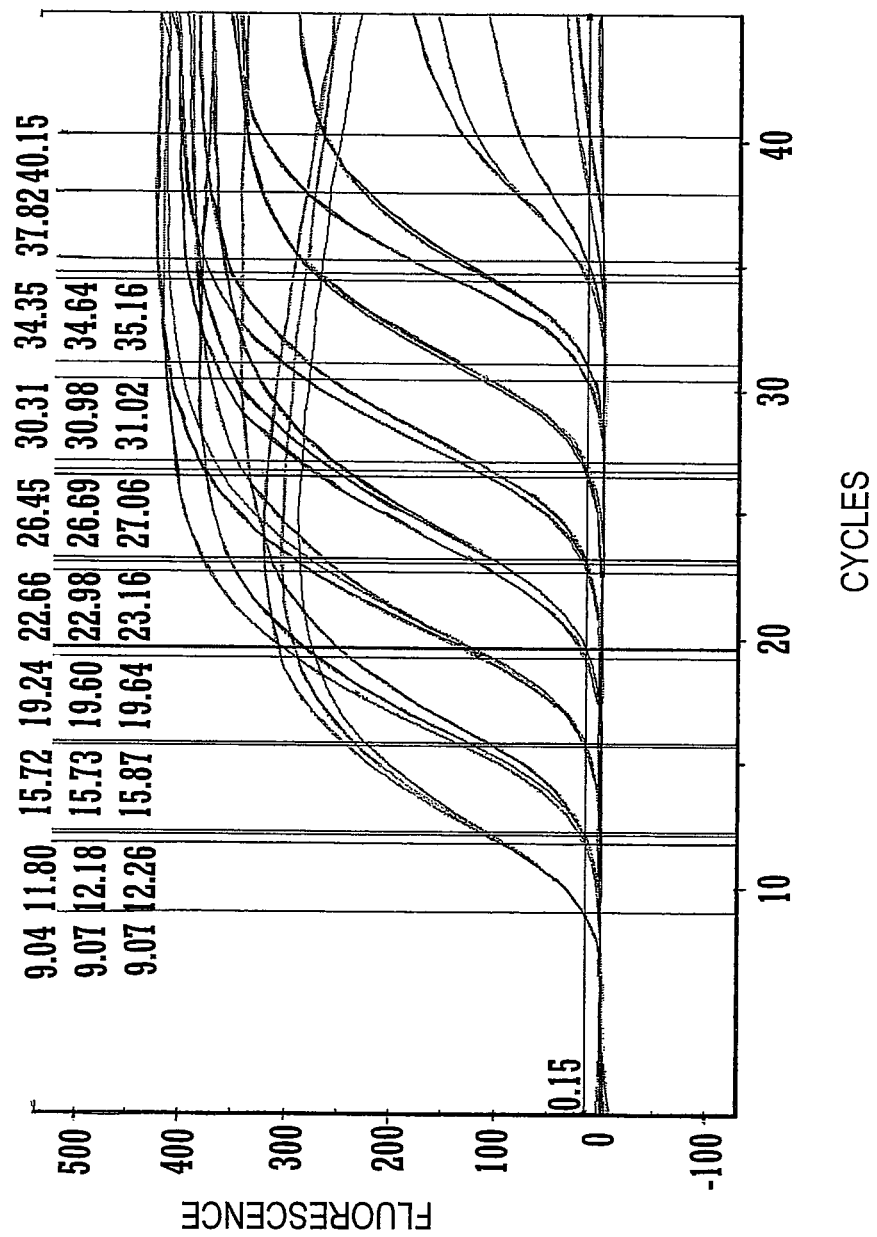
FIG. 2 is the standard curve established for the quantification of Norovirus Genogroup II using a TET-labeled oligonucleotide probe.
Figure 3:
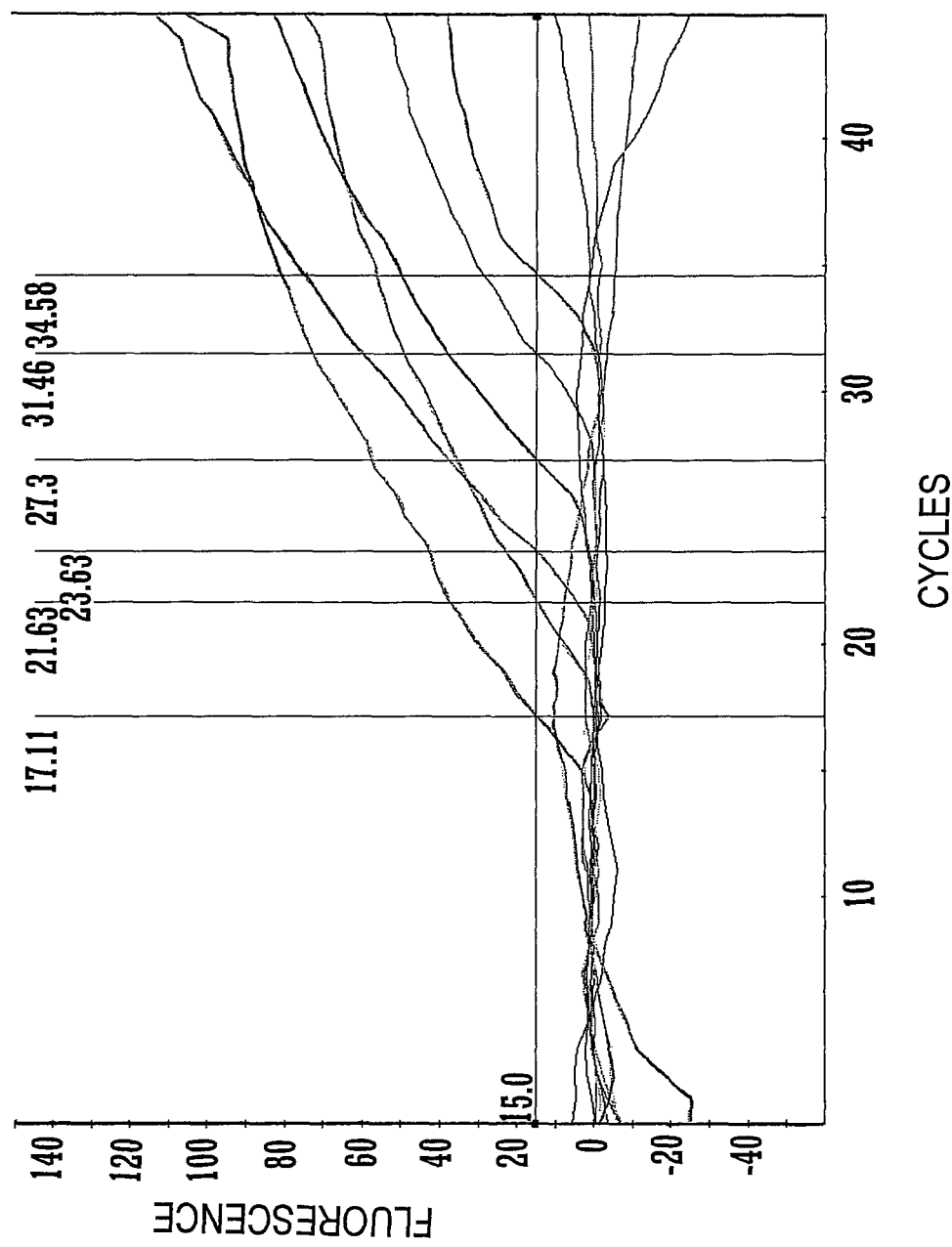
FIG. 3 is the standard curve established for the quantification of viruses from the Enterovirus group using a Cy5-labeled oligonucleotide probe.
Figure 4:
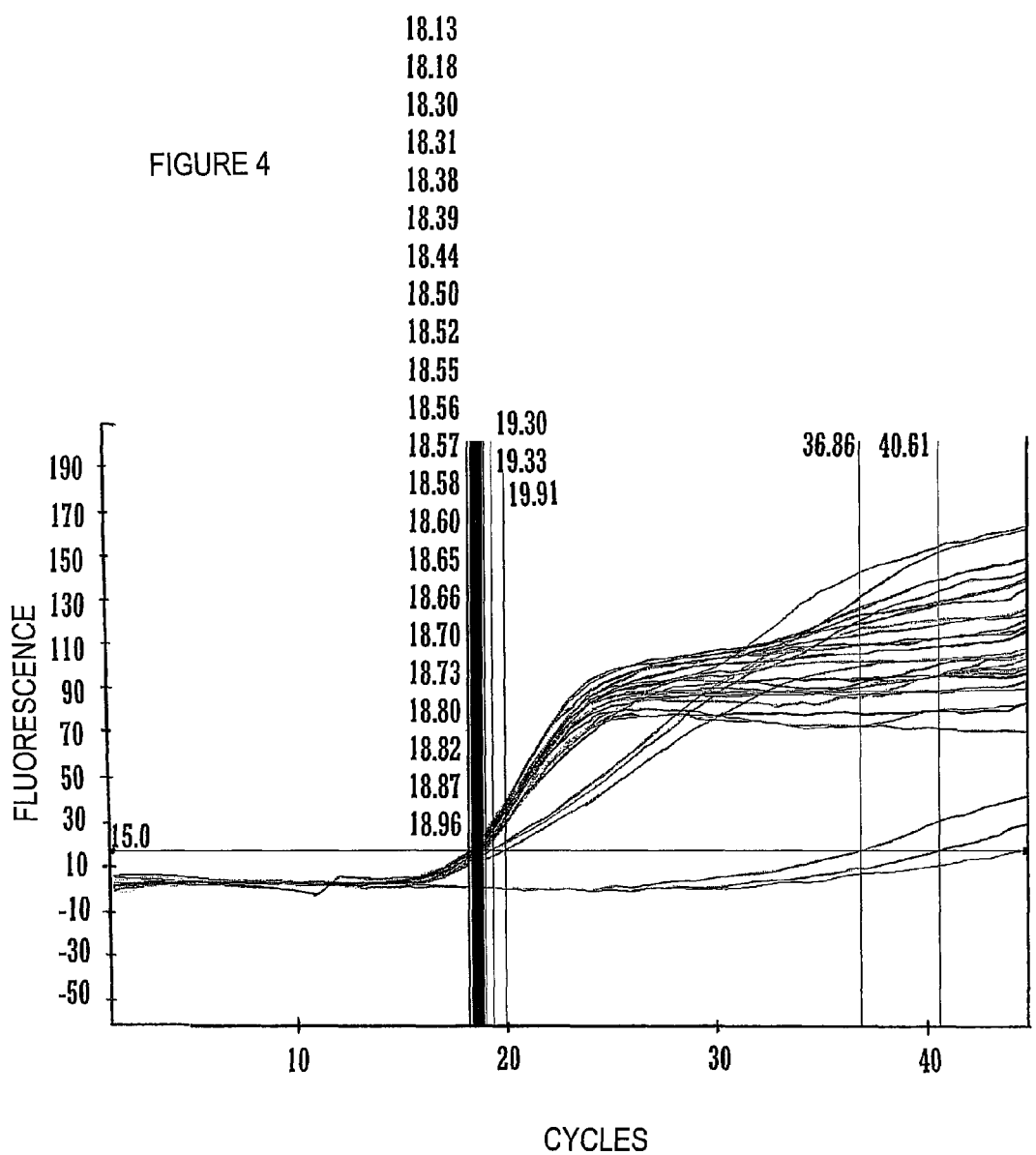
FIG. 4 is the standard curve established for the internal RNA control using a TxR-labeled oligonucleotide probe.

The term "biological sample" refers to a body sample from any animal, but preferably is from a mammal, more preferably from a human. Such samples include biological fluids such as serum, plasma, vitreous fluid, lymph fluid, synovial fluid, follicular fluid, seminal fluid, amniotic fluid, milk, whole blood, urine, cerebro-spinal fluid, saliva, sputum, tears, perspiration, mucus, and tissue culture medium, as well as tissue extracts such as homogenized tissue, and cellular extracts.

As used herein, "buffer" refers to a buffered solution that resists changes in pH by the action of its acid-base conjugate components. Buffers may optionally comprise a salt such as $MgCl_2$, $MnCl_2$, or the like. Buffers may also optionally comprise other constituents to improve the efficiency of reverse transcription or amplification, including, but not limited to, betaine, bovine serum albumin, etc.

The term "cDNA" refers to a complementary DNA molecule synthesized using a ribonucleic acid strand (RNA) as a template. The RNA may be mRNA, tRNA, rRNA, or another form of RNA, such as viral RNA. The cDNA may be single-stranded, double-stranded or may be hydrogen-bonded to a complementary RNA molecule as in an RNA/cDNA hybrid.

The term "Enterovirus group" refers to icosahedral, non-enveloped, single-stranded, positive-sense RNA viruses of the family Picornaviridae. The Enterovirus group is subdivided into poliovirus, coxsackievirus (Groups A and B), echovirus, and enterovirus. Enteroviruses cause a myriad of clinical pathologies in humans, including gastroenteritis. As used herein, "Enterovirus group" refers to the genus, and "enterovirus" refers to the enterovirus species that is part of the Enterovirus group.

The term "food sample" refers to a substance that is ingested by an animal, preferably a human. Food sample includes, but is not limited to, water, shellfish (e.g., bivalve molluscan shellfish such as oysters, mussels, and clams), and bakery products.

The term "Hepatitis A Virus" or "HAV" refers to a single stranded, positive-sense RNA virus of the family Picornaviridae. Hepatitis A or type A viral hepatitis was also formerly known as any of the following: infectious hepatitis, epidemic hepatitis, epidemic hepatitis, epidemic jaundice, catarrhal jaundice, infectious icterus, Botkins disease, and MS-1 hepatitis. Hepatitis A is usually self-limiting and produces the acute symptoms of fever, malaise, nausea, and abdominal discomfort followed by an extended period of jaundice. The minimum infectious dose is unknown but hypothesized to be between 10 and 100 virions. Hepatitis A is primarily transmitted via the fecal-oral route. Usually, persons infected in outbreaks acquire the disease through the ingestion of contaminated food, mostly water, shellfish, and salads.

The term "internal control" refers to a non-competitive universal RNA internal control, also referred herein as an internal control nucleic acid molecule, an internal control molecule, or a universal internal RNA control. The invention provides an internal control nucleic acid molecule including at least one forward primer annealing site, at least one reverse primer annealing site, and at least one amplifiable region, wherein the forward primer annealing site, the reverse primer annealing site, and the amplifiable region are all randomly generated. The internal control is also described in pending in PCT/US2004/015175, filed May 14, 2004, which claims priority to U.S. Provisional Application No. 60/471,121, filed May 16, 2003, hereby incorporated by reference.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin).

The term "Norovirus", formerly called small round-structured viruses or Norwalk-like viruses, refers to nonenveloped, single-stranded, positive-sense RNA viruses of the family Caliciviridae. The genus Norovirus is genetically divided into two genogroups, genogroup 1 and genogroup 2 (Ando et al., 2000, *J. Infect. Dis.,* 181: S336-S348; Katayama et al., 2002, *Virol.,* 299: 225-239). In humans, Noroviruses cause acute gastroenteritis.

The term "oligonucleotide" refers to a single-stranded nucleic acid including at least between two and about 100 natural or modified nucleotides or a mixture thereof. The oligonucleotide can be derived from a natural nucleic acid or produced by chemical or enzymatic synthesis.

"Polymerase chain reaction" or "PCR" refers to a procedure or technique in which minute amounts of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor Symp. Quant. Biol., 51:263 (1987); Erlich, ed., PCR Technology, (Stockton Press, N.Y., 1989).

The term "Reverse transcription polymerase chain reaction" or "RT-PCR" refers to the transcription of cDNA from a RNA template by the enzyme reverse transcriptase. The cDNA is then amplified by known PCR methods described above.

The term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

The term "probe" refers to an oligonucleotide that hybridizes to a target sequence. In the TagMan® or TaqMan -style assay procedure, the probe hybridizes to a portion of the target situated between the annealing site of the two primers. A probe can further include a detectable label, e.g., a fluorophore (Texas-Red®, Fluorescein isothiocyanate, etc.,). The detectable label can be covalently attached directly to the probe oligonucleotide, e.g., located at the probe's 5' end or at the probe's 3' end. A probe including a fluorophore may also further include a quencher, e.g., Black Hole Quencher™, Iowa Black™, etc. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides.

The term "quenching" refers to a decrease in fluorescence of a fluorescent detectable label caused by energy transfer associated with a quencher moiety, regardless of the mechanism.

The term "reaction mixture" or "PCR reaction mixture" or "RT-PCR reaction mixture" or "master mix" or "master mixture" refers to an aqueous solution of constituents in a PCR or RT-PCR reaction that can be constant across different reactions. An exemplary RT-PCR reaction mixture includes buffer, a mixture of deoxyribonucleoside triphosphates, reverse transcriptase, primers, probes, and DNA polymerase. Generally, template RNA or DNA is the variable in a PCR or RT-PCR reaction.

The term "reverse transcriptase" refers to a class of polymerases characterized as RNA-dependent DNA polymerases. All known reverse transcriptases require a primer to synthesize a DNA transcript from an RNA template. Historically, reverse transcriptase has been used primarily to transcribe mRNA into cDNA, which can then be cloned into a vector for further manipulation.

The term "rotavirus" refers to a segmented RNA virus of the family Reoviridae. The genome comprises 11 double-stranded RNA segments surrounded by three concentric layers of protein. Rotaviruses have been classified into six serological groups. Three of the serological groups infect humans (groups A, B, and C). Rotaviruses are usually transmitted via the fecal-oral route. Direct transmission between persons can occur, e.g., day care centers, family homes, and food contaminated by food handlers. Rotaviruses usually cause acute gastroenteritis, particularly in infants and children. Other names for gastroenteritis caused by rotaviruses include infantile diarrhea, winter diarrhea, acute nonbacterial infectious gastroenteritis, and acute viral gastroenteritis.

The term "specific for [a virus]" as applied herein to a primer or an oligonucleotide probe refers to a primer or oligonucleotide probe affective for annealing to its target polynucleotide and thereby producing (e.g., through RT-PCR or PCR) a detectable signal in the presence of said target polynucleotide without unacceptable levels of signal resulting from the annealing of the primer or oligonucleotide probe to a non-target polynucleotide.

The term "water sample" refers to a sample collected from a water source. The water source includes, but is not limited to, surface water (lakes, rivers, reservoirs, oceans, etc.), groundwater, wastewater (i.e., sewage), recreational water (water used for the purpose of recreation, i.e., swimming pool, spa, waterparks, etc.), and finished water (delivered to a distribution system after treatment, if any). Water can be either treated or untreated. Treated water has undergone a disinfection process (e.g., chlorination, filtration) for the purpose of making it safe.

Methods and Reagents for Detecting or Quantifying Norovirus and/or Enterovirus

The present invention includes a method for detecting Norovirus genogroups I and II, and optionally Enteroviruses, in a single reaction mixture. The reaction mixture can include a universal internal RNA control. In an embodiment, advantageously, the method of the invention can discriminate between Norovirus genogroup I and II in a single reaction mixture. In an embodiment, the method of the invention can detect Norovirus genogroup I and II in a single reaction mixture. In an embodiment, the method of the invention can quantify Norovirus genogroup I and II in a single reaction mixture. Existing assays cannot accomplish this. Additionally, in an embodiment, the present method can employ the universal internal control to provide one or more advantages. These advantages include, for example, establishing a single standard curve for detection and/or quantification, normalizing data in each individual reaction, determining whether the conditions (i.e., cycling conditions, primer/probe concentrations, salt concentrations, etc.) within the reaction were suitable or optimal, and if or to what extent inhibitory materials or excessive target template were present.

In an embodiment, the present method can employ or be a single reaction mixture, which can be suitable for all of a set of samples. The reaction mixture can be aliquotted into different PCR tubes and template RNA added (or omitted for a negative control). The template RNA can be from an unknown sample suspected of including RNA from a Norovirus or Enterovirus. Thus, the template RNA can be the variable amongst the different PCR tubes. The RT-PCR reaction mixtures can contain buffer, reverse transcriptase, DNA polymerase, and dNTPs.

In an embodiment, the present reaction mixture can include at least one of: primers specific for Norovirus Genogroup I, primers specific for Norovirus Genogroup II, an oligonucleotide probe(s) specific for Norovirus Genogroup I, an oligonucleotide probe(s) specific for Norovirus Genogroup II, an internal control nucleic acid molecule, primers specific for said universal internal RNA control, and an oligonucleotide probe(s) for said universal internal RNA control. Optionally, the reaction mixture can also include primers specific for a RNA virus and an oligonucleotide probe(s) specific for a RNA virus. The RNA virus to be detected and quantified can be Hepatitis A virus, Rotavirus, or a virus of the Enterovirus group, such as poliovirus, echovirus, enterovirus, or coxsackievirus. A suitable oligonucleotide probe can include a detectable label, a quencher moiety, or both.

A suitable concentration range of the viral RNA primers in the reaction mix is between about 200 nM and about 500 nM. A suitable concentration range of the primers for the internal control nucleic acid molecule in the reaction mix is between about 50 nM and about 200 nM. A suitable concentration range of the oligonucleotide probes to hybridize to viral amplification products in the reaction mix is between about 50 nM and about 400 nM. A suitable concentration range of the primers for the internal control nucleic acid molecule in the reaction mix is between about 50 nM and about 250 nM, more preferably between about 75 nM and about 200 nM. Specific concentrations may perform better than other concentrations depending upon RT-PCR conditions and the template to be amplified.

PCR tubes with aliquots of reaction mixture described above can be kept on ice and RNA template added. The individual PCR tubes can be placed in a thermal cycler, preferably with a hot start, and reverse transcription and amplification can proceed. Known and commercially available instrumentation and software can then detect and quantify virus in each PCR tube.

Virus Samples

The present method can operate on any of a variety of samples suspected containing a viral RNA, such as a Norovirus RNA and/or an Enterovirus RNA. The sample can be collected from any of a variety of sources suspected of being contaminated with Norovirus and/or an Enterovirus. In an embodiment, the sample can be from a body of water, food, a food processing surface, a biological sample, or the like. The present method can include collecting the sample. Common vectors for enteric virus infection include bivalve molluscan shellfish, which can become contaminated by bio-accumulating virus from polluted waters.

In an embodiment, the virus or viral RNA can be isolated or recovered prior to conducting RT-PCR. Virus or viral RNA can be separated and concentrated from a sample by any of a variety of well known methods, such as, elution, precipitation (e.g., PEG), solvent extraction (e.g., chloroform, ether, etc.), ultracentrifugation, ultrafiltration, antigen-antibody capture, nucleic acid extraction, and the like. Such methods can be employed, for example, on shellfish tissue. These and similar methods can be used to extract virus or viral RNA from any of a variety of samples.

RT-PCR

Reverse transcriptases have been extensively used in reverse transcribing RNA prior to PCR amplification, otherwise known as reverse transcription polymerase chain reaction (RT-PCR). RT-PCR, such as real-time RT-PCR, is known. Any of a variety of published protocols can be used (and modified as needed) for use in the present method. Suitable RT-PCR procedures include those presented in U.S. Pat. No. 5,618,703, which is hereby incorporated by reference.

Briefly, RT-PCR includes three basic steps: (1) denaturating RNA and hybridizing the reverse primer; (2) synthesis of cDNA; and (3) PCR amplification. RT-PCR can be performed by an uncoupled or coupled procedure. In an uncoupled RT-PCR, reverse transcription is performed independently from the PCR amplification in separate reactions. Whereas, continuous RT-PCR is performed in a single reaction tube using a common reaction mixture including both the reverse transcriptase and the DNA polymerase. The methods of the invention encompass all versions of RT-PCR.

For primer extension to occur, the primer anneals to the RNA template. Not every nucleotide of the primer need anneal to the template for reverse transcription to occur. The primer sequence need not reflect the exact sequence of the template. For example, a non-complementary nucleotide fragment may be attached to the 5' end of the primer with the remainder of the primer sequence being complementary to the RNA. Alternatively, non-complementary bases can be interspersed into the primer, provided that the primer sequence has sufficient complementarity with the RNA template for hybridization to occur and allow synthesis of a complementary DNA strand. Thus, the embodiments of the invention contemplate variants of the primers described herein.

Reverse transcriptase enzymatic activity provides a cDNA transcript from an RNA template. The methods for production and amplification of DNA segments from an RNA molecule where the RNA molecule is a member of a population of total RNA or is present in a small amount in a biological sample are well known. In sum, DNA amplification procedures by PCR are well known and are described in U.S. Pat. No. 4,683,202. In PCR, the primers anneal to the target nucleic acid at sites distinct from one another and in an opposite orientation. A primer annealed to the target sequence is extended by the enzymatic action of a DNA polymerase. The extension product is then denatured from the target sequence, and the process is repeated. Successive cycling of this procedure provides amplification at a logarithmic rate.

There are many reverse transcriptases (e.g., Moloney Murine Leukemia Virus (M-MuLV) Reverse Transcriptase from New England Biolabs, Inc., Beverly, Mass.; HIV reverse transcriptase from Ambion, Inc., Austin, Tex.) and DNA polymerases (e.g., Taq and T7 DNA polymerases from New England Biolabs, Inc.; Pfu DNA polymerase from Promega, Inc., Madison, WI) that are commercially available. The methods of the invention are not limited to any particular enzyme, although some enzymes may be preferable under specific conditions.

Real-Time RT-PCR

Real-time PCR allows automated quantification of reaction product for each sample per cycle. Commonly used instrumentation and software products perform the quantification calculations automatically. The quantification has a broad $10^7$-fold dynamic range that is possible, but usually, the dynamic range is closer to 2-3 logs. The recent advancement in PCR instrumentation technology, e.g., Cepheid's Smart Cycler® II, allows the simultaneous detection and quantification of fluorescent signals in up to four different channels in real-time. In addition, the latest generation of thermal cyclers are designed to maximize dye excitation providing a more accurate means of detecting fluorescence. Thus, multiple amplification products can be assessed in the same reaction mixture and quantified more accurately. Further, each reaction site can be programmed independently, thereby starting the reaction independent of other reactions. Thus, samples can be evaluated as needed and do not have to wait for the completion of a programmed reaction already in progress. Therefore, this new technology now allows for the detection and quantification of multiple targets in a single sample in real-time There are four different probe systems in current use for real-time PCR-Molecular Beacons (Sigma-Genosys, Inc., The Woodlands, Tex.), Scorpions® (DxS Ltd., Manchester, UK), SYBR® Green (Molecular Probes, Eugene, Oreg.), and TaqMan® (Applied Biosystems, Foster City, Calif.). These four systems employ fluorescent labels that the instrumentation detects fluorescence and the software interprets levels of fluorescence.

SYBR® Green is a fluorescent dye that only strongly fluoresces when bound to double stranded DNA. As mentioned above, SYBR® green assays, while useful for detection, are not reliable in quantification of template concentration due to its non-specific intercalation into any double stranded DNA (primer-dimer and products of non-specific amplification). Thus, SYBR® Green provides a quick method of detection, but is not reliable for quantification. As a result, further assays are required to confirm the quantification of reaction product.

Molecular Beacons, Scorpions®, and TaqMan® utilize Förster Resonance Energy Transfer (FRET) by coupling a fluorescent label with a quencher moiety. A fluorescent label is covalently bound to the 5' end of an oligonucleotide probe, while the 3' end has a quencher moiety attached. These oligonucleotide probes are site specific to hybridize to the amplified product. Preferably, the oligonucleotide probes are designed to hybridize to a central region of the amplified product. For TaqMan® assays, the 5'-nuclease activity of the DNA polymerase cleaves the probe during the replication cycle. Due to the cleavage of the probe, the quencher moiety is no longer coupled to the fluorescence label and cannot quench fluorescence. Fluorescence thus represents replicating DNA.

Similarly, Molecular Beacons utilizes an oligonucleotide probe with a fluorescent label attached to the 5' end and a quencher moiety attached to the 3' end. When free in solution, the Molecular Beacons oligonucleotide probe forms a hairpin structure. In the hairpin structure, the quencher moiety is able to quench fluorescence due to FRET. However, during PCR, the oligonucleotide probe unfolds and hybridizes to its complementary DNA, and the quencher is no longer close enough to the fluorescent label to quench fluorescence. Thus, fluorescence reports the hybridization between an oligonucleotide probe and its specific target cDNA. However, Molecular Beacons are not accurate in quantifying the reaction product due to competition from PCR product synthesis. In this system, target/complement reannealing and target strand folding provide competition for the site of Molecular Beacon hybridization.

Scorpions® also utilize an oligonucleotide probe with a fluorescent label attached to the 5' end and a quencher moiety attached to the 3' end in a hairpin structure free in solution. However, the Scorpions® oligonucleotide probe also serves as a primer. The Scorpions® oligonucleotide probe/primer extends from the hairpin loop structure and hybridizes to the target. The Scorpions® oligonucleotide probe/primer fluoresces, and the DNA polymerase extends the target DNA from the primer. Thus, the probe detects the extension product, whish is its own primer-unimolecular rearrangement. Thereby, the fluorescence reports the extension and thus copy number of reaction product.

In an embodiment, the present method employs TaqMan -style probes (dual-labeled probes to fluoresce upon 3' exonuclease activity). In certain embodiments, the TaqMan®-style probes can be advantageous compared to, for example, SYBR® Green probes. Although not limiting to the present invention, this may be due to the ability to more accurately quantify the amplification products.

In an embodiment, the present method employs TaqMan -style probes and oligonucleotides that selectively hybridize to Norovirus Genogroup I or Norovirus Genogroup II (SEQ ID NOs: 3, 4, and 7). In an embodiment, the Norovirus Genogroup I probes can be coupled to 6-carboxyfluorescein at the 5' end of the oligonucleotide, and the Norovirus Genogroup II probe can be coupled to tetracholoro-6-carboxyfluorescein at the 5' end. In an embodiment, the oligonucleotide can also be coupled to a quencher moiety at the 3' end. A preferred quencher moiety for the Norovirus probes is Black Hole Quencher™ (Biosearch Technologies, Novato, Calif.). The oligonucleotide probes exemplified by SEQ ID NOs: 3 and 4 selectively bind to the amplification product of Norovirus Genogroup I. Suitable instrumentation will thereby detect the fluorescence produced from the cleavage of the oligonucleotide probe by the nuclease activity of the DNA polymerase during replication. Analysis software then determines the quantity of amplification product based upon the fluorescence data.

Similarly, an embodiment of the invention can use the oligonucleotide probe of SEQ ID NO:10 to selectively hybridize to viruses of the Enterovirus group, This probe can be coupled to cyanin5 (Amersham Biosciences Corp., Piscataway, N.J.) at the 5' end and Iowa Black (Integrated DNA Technologies, Coralville, Iowa) at the 3' end. Additionally, an embodiment of the invention can use the oligonucleotide probe of SEQ ID NO:13 to hybridize to a internal control nucleic acid. This probe can be coupled to Texas Red at the 5' end and Iowa Black at the 3' end.

Quantification of PCR Results
Standard Curve

A standard curve can be generated from an RNA of known concentration. The standard curve can then be used to determine RNA levels (copy number) of unknown concentrations. Prior to the development of the universal internal RNA control, use of a standard curve required laborious and uncertain steps. Previous methods incorporated the construction of plasmids containing the cDNA to be transcribed in vitro. The transcribed RNA would be the standard, but accurate quantification was difficult due to problems with stability.

Other nucleic acids besides RNA can be used to establish a standard curve. These methods are well known and include double stranded DNA, a cDNA expressing a target gene, or an in vitro generated single stranded DNA. Methods may vary according to the nucleic acid chosen to serve as the standard to establish a standard curve.

Comparative Cycle Threshold

The comparative cycle threshold (Ct) method, also known as the $2^{-\Delta\Delta Ct}$ method, is also used to quantify RNA levels. The Ct method compares a test reaction with a control or calibrator sample. The Ct values of both the control/calibrator sample and the test sample are normalized. In an embodiment of the invention, the Ct values were normalized to an arbitrary cutoff, 20-22. In another embodiment, the Ct values were normalized to within 1 Ct value of a negative control (a sample with no inhibition). This allows for the sensitivity of the assay and proper dynamic range.

The Ct method can also be described by the formula $\Delta\Delta Ct = \Delta Ct_{test\ sample} - \Delta Ct_{reference\ sample}$. The amplification efficiencies of the test sample and the reference sample must be about the same for the formula to operate. Amplification efficiencies can be determined by a comparison of the samples with template dilution. The amplification efficiency is about the same when a plot of cDNA dilution versus $\Delta Ct$ approximates zero.

Universal Internal RNA Control

Internal control nucleic acid molecules in accordance with the invention can function as a part of a system to provide a method of eliminating false negatives during nucleic acid amplification procedures and/or associated detection methods. Internal control nucleic acid molecules can also function to provide a means to estimate the degree of PCR inhibition in reactions that make use of the quantitative capabilities of real-time PCR and RT-PCR. If a substance is present in a test sample matrix which inhibits or enhances the PCR amplification, the degree of inhibition or enhancement may be estimated and the quantitative data may be adjusted based upon shifts in the amplification characteristics (for example shifts in the real-time PCR Ct value) of the internal control.

The internal control nucleic acid molecule in accordance with the invention can function by providing a known amplifiable nucleotide for inclusion in a nucleic acid amplification procedure to ensure that the sample conditions are not inhibiting amplification of the nucleic acids. In addition, data obtained during amplification of the internal control may be used to estimate PCR inhibition and adjust quantitative data in quantitative assays.

Primers. An internal control nucleic acid molecule in accordance with an embodiment of the invention includes at least one forward primer annealing site, at least one reverse primer annealing site, and at least one amplifiable region.

In one embodiment of the invention, the forward primer annealing site and the reverse primer annealing site include from about 15 to about 25 base pairs each. In another embodiment of the invention, the forward primer annealing site and the reverse primer annealing site include from about 18 to about 24 base pairs each. In yet another embodiment, the forward primer annealing site and the reverse primer annealing site include from about 20 to about 23 base pairs each.

The amplifiable region is flanked by the forward primer annealing site on one end and by the reverse primer annealing site on the other end. The length of the amplifiable region, i.e., the region between the forward primer annealing site and the reverse primer annealing site can vary greatly from as little as about 15 base pairs to greater than about 1000 base pairs. The length of the amplifiable region can depend on a number of factors, including, but not limited to the length of the target genes that the nucleic acid amplification procedure is targeting.

There are a number of design characteristics that can be considered when generating the sequences. Examples of these considerations include, but are not limited to: the GC content of the sequence; a lack of identity to any known, naturally occurring sequences, or amplifiable region; and the lack of repetitive regions of the same base pair. The pseudo-randomly generated sequence can be designed by considering any combination of these various characteristics.

Internal control nucleic acid molecules can include deoxyribonucleic acid (DNA), and ribonucleic acid (RNA). One of skill in the art will also understand that once the internal control nucleic acid molecule has been designed, it can be made by any method commonly known and used by those of skill in the art. Alternatively, the internal control nucleotide molecule can be synthesized by a company such as Integrated DNA Technologies (Coralville, Iowa). It is also practical to synthesize this molecule in most molecular biology laboratories by combining specific synthesized oligonucleotides into a designated sequence.

Probes. In another embodiment of the invention, the internal control nucleic acid molecule also includes at least one probe hybridization region. The probe hybridization region can be configured to be complementary to a real-time PCR probe. The probe for which the probe hybridization region is complementary may be any probe that is commonly known and used in assays for DNA detection and/or quantification. The nucleotide sequence of the probe is designed to be complementary to a region of the internal control nucleic acid molecule of the invention that can be amplified by PCR using primers designed for use with the internal control nucleic acid molecule. If for example, probe A with a base pair sequence of ATCTCG is going to be used, the probe hybridization region would have a sequence of (for example) CGAGAT. The probe can be designed using specifications unique to each type of probe—typically using specialized software such as (for example) Primer Express (Applied Biosystems, Foster City, Calif.). The probe will behave much like a primer in terms of the hybridization of the probe to the internal control DNA sequence in that it is designed to hybridize to regions in the internal control nucleic acid molecule. These regions are unlikely to have nucleotide identity to regions internal to amplifiable regions in any naturally-occurring sequences for the same reasons described above for the primer annealing regions.

Examples of assays that may utilize a probe include, but are not limited to the 5' nuclease assay, which is known commercially as TaqMan® (Applied Biosystems). In the TaqMan® or a TaqMan®-style assay, a probe can be utilized that is designed to hybridize to a DNA sequence internal to the primers targeting a specific amplification region. The probe is typically labeled at the 5' end with a reporter molecule such as a fluorescent dye and a quencher molecule at the 3' end.

Detecting Inhibition. While a positive and negative control are normally run for every RT-PCR or PCR reaction mix to ensure the integrity of the reagents, inhibition of the PCR by the sample matrix may cause a falsely negative result. In quantitative real-time PCR this is even more of a concern, as partial PCR inhibition may lead to inaccurate quantification results. Therefore, it is desirable to include an internal positive control in each individual reaction to prevent the reporting of false negatives and to potentially allow accurate adjustments to quantitative data.

Some matrices contain inhibitors of PCR analysis (i.e., shellfish). Matrices high in glycogen or have excessive amounts of protein and/or DNA will inhibit amplification of a target RNA template. The amplification product of the RT-PCR of recovered RNA from one of these matrices will be logs away from the negative control. With the inclusion of a universal internal RNA control, viral RNA can be quantified within 1 or 2 logs by adjusting for the inhibition. The negative control allows for a normalization to an uninihibited sample.

Applications of the Present Method and Reagents

The applications of the invention are extensive. Provided the hardware and software capabilities, the method of the invention is relatively quick and easy to employ. The necessary hardware includes a computer, a PCR thermal cycler, and optics for fluorescence excitation and emission collection, plus capture and analysis software. Additionally, many biotechnology suppliers (i.e., Ambion, Inc.) manufacture RT-PCR kits for user ease. Therefore, the invention can be used at sites prone to enteric virus outbreak (i.e., cruise ships, food distribution centers) or at medical facilities (i.e., hospitals).

For instance, the instrumentation and the methods of the invention could be deployed on cruise ships to diagnose and possibly prevent large outbreaks. A passenger with acute gastroenteritis could provide a sample (e.g., stool sample) to a ship's physician or technician trained in the procedure. The etiologic agent can be detected in the patient sample. This same equipment and embodiments of the invention can also be used to detect, and thus isolate, the contaminated food source. Since more than one virus may be present in detectable levels, a determination of the copy number of virus present in the contaminated food source will also help to correctly determine the etiologic agent of gastroenteritis or any other ailments. Besides rehydration, patients suffering from Norovirus can be treated with bismuth sulfate (Center for Disease Control and Prevention, 2001, *Morb. Mortal. Wkly. Rep.*, 50(RR02): 1-69). The invention described herein can be used to provide a relatively quick diagnosis and assessment of enteric virus infection or contamination.

In another application, the food industry could test commonly contaminated food products for enteric viruses by utilizing the invention described herein. A technician could test food samples (i.e., shellfish) for the presence of enteric virus. Additionally, a technician could also quantify the level of enteric virus present. By quantifying the virus levels, a technician could determine whether contaminated food is above or below the threshold for a minimum infectious dose.

Embodiments of the Current Invention

An embodiment of the current invention includes a method of reverse transcription-polymerase chain reaction (RT-PCR), which includes a) amplifying a reverse transcribed cDNA in a mixture including oligonucleotide probes and primers specific for Norovirus Genogroup I and Norovirus Genogroup I; b) quantifying virus; and c) normalizing data to amplification of a universal internal RNA control in the same reaction mixture. Optionally, the method may include a step of detecting another RNA virus or virus group, including Rotavirus and positive RNA strand virus, such as Hepatitis A virus (HAV) and Enterovirus group (i.e., poliovirus, enterovirus, echovirus, and coxsackievirus). The internal control nucleic acid molecule used in the RT-PCR reaction mixture may include SEQ ID NO: 14. The method may include at least one primer of SEQ ID NOs: 1, 2, 5, 6, 8, 9, 11, and 12. The method may also include at least one oligonucleotide probe of SEQ ID NOs: 3, 4, 7, 10, and 13. Samples to be tested for the presence and quantity of RNA include a biological sample (e.g., blood, urine or stool), a food sample (e.g., shellfish such as oysters, clams and mussels), and a water sample (e.g., wastewater, groundwater, ocean water, lake water, river water, or recreational water).

Another embodiment of the current invention is a RT-PCR reaction including a) an oligonucleotide probe and primers specific for Norovirus Genogroup I; b) an oligonucleotide probe and primers specific for Norovirus Genogroup I; c) a universal internal nucleic acid molecule, wherein said molecule contains at least one forward primer annealing site, at least one reverse primer annealing site, and at least on amplifiable region; d) a universal internal control oligonucleotide probe; and e) a universal internal control primers. The primers and oligonucleotide probes may include at least one of the polynucleotides of SEQ ID NOs: 1-7 and 11-13. The internal control nucleic acid molecule may also include the polynucleotide of SEQ ID NO:14. Another embodiment of the invention includes, the reaction mixture, including the primers and oligonucleotide probes discussed herein, packaged together as a kit, which may or may not include instructions for use.

The present invention may be better understood with reference to the following examples. These examples are intended to be representative of specific embodiments of the invention, and are not intended as limiting the scope of the invention.

EXAMPLES

Example 1

Development of a Quantitative Multiplex RT-PCR Assay for the Detection of Noroviruses and Enteroviruses The use of RT-PCR based assays has increased detection sensitivity of Enteroviruses and reduced analysis time. The predominant human Noroviruses, which are placed into two genogroups, GI and GII, have not been cultured. Thus, Norovirus detection is based primarily upon non-quantitative RT-PCR assays. To date, no single assay has been capable of simultaneous detection and enumeration of GI genogroup Norovirus and GII genogroup Norovirus.

In the present study, a multiplex qRT-PCR assay using the Cepheid SmartCycler® (Cepheid, Sunnyvale, Calif.) system has been developed for the simultaneous detection and quantification of viruses from the Enterovirus genus. The following example demonstrated that the multiplex qRT-PCR can simultaneously detect Enterovirus, Norovirus genogroup I, and Norovirus genogroup II. The assay also incorporated a novel quantitative universal internal control to prevent the reporting of false negatives due to inhibition or failure of the qRT-PCR. The development of this methodology allows the rapid semi-quantitative determination of Norovirus and Enterovirus levels.

Methods

A. Reverse Transcription of RNA Templates

RNA was isolated and purified by known methods from a GI Norovirus (Norwalk virus strain 8FIIa), a GII Norovirus isolated from the stool of an ill individual (93% homologous to Lordsdale strain), and human Polio virus 3 (Sabin Strain). The isolated GI Norovirus, GII Norovirus, and Polio virus RNA were reverse transcribed and amplified by RT-PCR using the QIAGEN® OneStep RT-PCR Kit (Qiagen, Valencia, Calif.). Briefly, template RNA was added to a RT-PCR reaction mixture of QIAGEN OneStep RT-PCR Buffer (Tris·Cl/KCl/(NH$_4$)SO$_4$, 12.5 mM MgCl$_2$, DTT; pH 8.70), 400 µM of each dNTP (dATP, dCTP, dGTP, and dTTP), 1.25 U of Super RNasin (Ambion), primers and probes (see Tables 1-5), the internal control nucleic acid molecule (SEQ ID NO: 14) and QIAGEN OneStep RT-PCR Enzyme Mix containing Omniscript® reverse transcriptase, Sensiscript® reverse transcriptase, and HotStarTaq DNA polymerase. A negative control was included that did not contain template RNA. Each sample was tested in triplicate.

TABLE 1

GI Norovirus Primers and Probes

| Primer/Probe | SEQ ID NO. | Sequence (5'→3') |
|---|---|---|
| COG1F | 1 | CGYTGGATGCGNTTYCATGA |
| COG1R | 2 | CTTAGACGCCATCATCATTYAC |

TABLE 1-continued

GI Norovirus Primers and Probes

| Primer/Probe | SEQ ID NO. | Sequence (5'→3') |
|---|---|---|
| GI-P-1 | 3 | AGATYGCGATCYCCTGTCCA |
| GI-P-1b | 4 | AGATCGCGGTCTCCTGTCCA |

TABLE 2

GII Norovirus Primers and Probes

| Primer/Probe | SEQ ID NO. | Sequence (5'→3') |
|---|---|---|
| COG2F | 5 | CARGARBCNATGTTYAGRTGGATGAG |
| COG2R | 6 | TCGACGCCATCTTCATTCACA |
| GII-P | 7 | TGGGAGGGCGATCGCAATCT |

Y is C or T; R is A or G; B is C, G, or T; and N is A, C, G, or T.

TABLE 3

Enterovirus Primers and Probes

| Primer/Probe | SEQ ID NO. | Sequence (5'→3') |
|---|---|---|
| EV1F | 8 | CCTCCGGCCCCTGAATG |
| EV4R | 9 | CACCGGATGGCCAATCCAA |
| EV-P | 10 | CGGACACCCAAAGTAGTCGGTTCCG |

TABLE 4

Universal Internal RNA Control Primers and Probes

| Primer/Probe | SEQ ID NO. | Sequence (5'→3') |
|---|---|---|
| IC-46F | 11 | GACATCGATATGGGTGCCG |
| IC-194R | 12 | AATATTCGCGAGACGATGCAG |
| IC-P | 13 | TCTCATGCGTCTCCCTGGTGAATGTG |

The reporter dye 6-carboxyfluorescein (FAM; Integrated DNA Technologies, Coralville, Iowa) was coupled to the 5' end of probes GI-P-1 and GI-P-1b; tetrachloro-6-carboxyfluorescein (TET; Integrated DNA Technologies) was coupled to the 5' end of probe GII-P; cyanin 5 (Cy5™; Amersham Biosciences Corp., Piscataway, N.J.) was coupled to the 5' end of probe EV-P; and Texas Red® (TxR; Integrated DNA Technologies) was coupled to the 5' end of the universal internal RNA control probe. Black Hole Quencher™ 1 (BHQ1; Biosearch Technologies, Novato, Calif.) was coupled to the 3' end of probes GI-P-1, GI-P-1b, and GII-P, and Iowa Black™ (Integrated DNA Technologies) was coupled to the 3' end of probe EV-P and IC-P.

TABLE 5

Primer and Probe Concentrations in the Master Mix

| | Concentration |
|---|---|
| Primer | |
| COG1F (SEQ ID NO: 1) | 300 nM |
| COG1R (SEQ ID NO: 2) | 300 nM |
| COG2F (SEQ ID NO: 5) | 300 nM |
| COG2R (SEQ ID NO: 6) | 300 nM |
| EV1F (SEQ ID NO: 8) | 400 nM |
| EV1R (SEQ ID NO: 9) | 400 nM |
| IRC-46F (SEQ ID NO: 11) | 75 nM |
| IRC-194R (SEQ ID NO: 12) | 75 nM |
| Probes | |
| GI-P-1 (SEQ ID NO: 3) | 100 nM |
| GI-P1b (SEQ ID NO: 4) | 100 nM |
| GII-P (SEQ ID NO: 7) | 100 nM |
| EVP (SEQ ID NO: 10) | 300 nM |
| IC-P (SEQ ID NO: 13) | 150 nM |

Using a hot start, the samples were kept on ice until the Cepheid SmartCycler® reached its initial cycling temperature of 50° C. and then the PCR tubes were placed in the thermal cycler. The samples were incubated at 50° C. for 3000 sec followed by HotStartTaq™ DNA Polymerase activation at 95° C. for 900 sec. These incubations in the thermal cycler were followed by 45 cycles of 95° C. for 10 sec, 53° C. for 25 sec, and 62° C. for 70 sec. Fluorescence was read at the end of each elongation step. The resulting amplicons were also visualized by 4% TAE gel electrophoresis.

B. Optics Graphs

The fluorescence intensity of each RT-PCR reaction was plotted against PCR cycles. Cycle threshold (Ct) values are the number of cycles required for the fluorescence intensity graph to cross an arbitrary threshold. The Ct value for the reactions was 15.0. Data were collected, viewed, and graphed using the SigmaPlot® 2000 (SPSS Inc., Chicago, Ill.).

Results and Discussion

Advancements in real-time quantitative RT-PCR (qRT-PCR) technology have allowed the recent development of several qRT-PCR assays for the rapid detection and enumeration of enteroviruses, and specifically Norovirus. However, the TaqMan® style assays developed for Norovirus detection requires separate simplex reactions to distinguish the GI and GII genogroups (Kageyama et al., 2003). Additionally, the SYBR® Green RT-PCR assay has two distinct disadvantages-1) the assay is unable to reliably distinguish these two genogroups, and 2) is not be reliable in the quantification of template concentration due to its non-specific intercalation into double stranded DNA to produce primer-dimers and other non-specific amplification.

Figure 5:
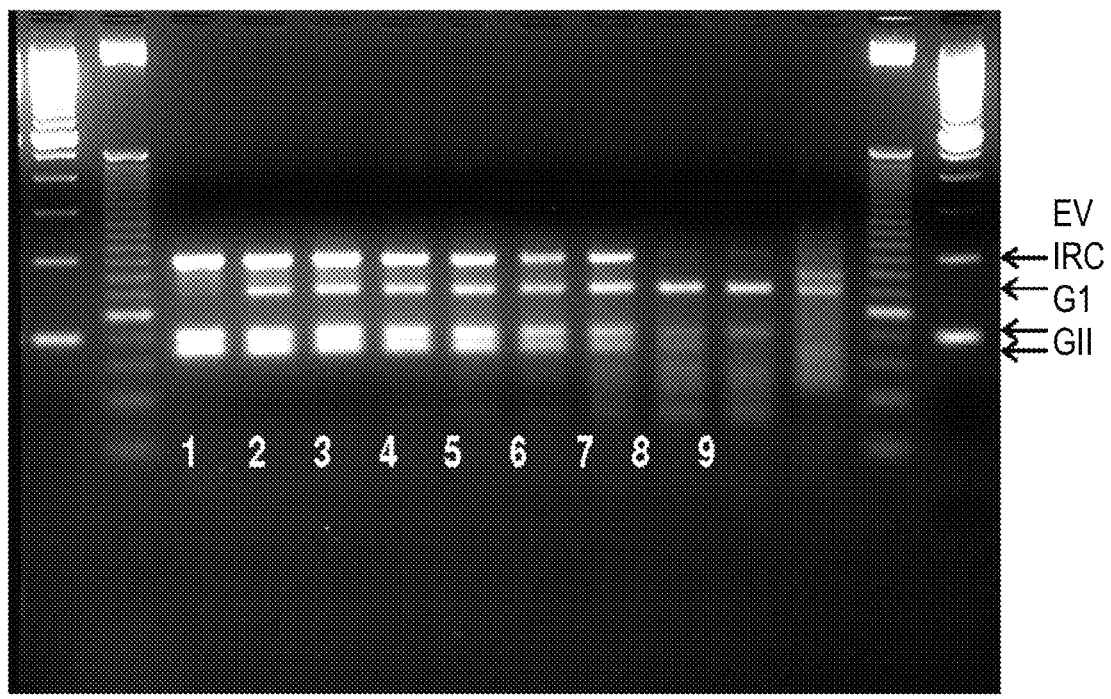
FIG. 5 is a 4% TAE agarose gel to determine the effect of template overload. Lane 1-10° dilution; Lane 2-$10^{-1}$ dilution; Lane 3-$10^{-2}$ dilution; Lane 4-$10^{-3}$ dilution; Lane 5-$10^{-4}$ dilution; Lane 6-$10^{-5}$ dilution; Lane 7-$10^{-6}$ dilution; Lane 8-$10^{-7}$ dilution; Lane 9-$10^{-8}$ dilution; Also shown is a negative control lacking viral template RNA, a 100 by ladder (Invitrogen, Inc., Carlsbad, Calif.), and a 25 by ladder (Invitrogen).

The multiplex qRT-PCR assay was able to simultaneously detect Enterovirus group viruses, Norovirus GI, Norovirus GII, and the internal control nucleic acid molecule (FIGS. 1-4). The assay had a dynamic range of greater than seven logs. The resulting PCR products were run on a 4% TAE gel. Amplicons were observed at the predicted target size for Norovirus GI (84 bp), Norovirus GII (97 bp), Enterovirus (196 bp), and the universal internal RNA control (149 bp) (FIG. 5).

Figure 6:
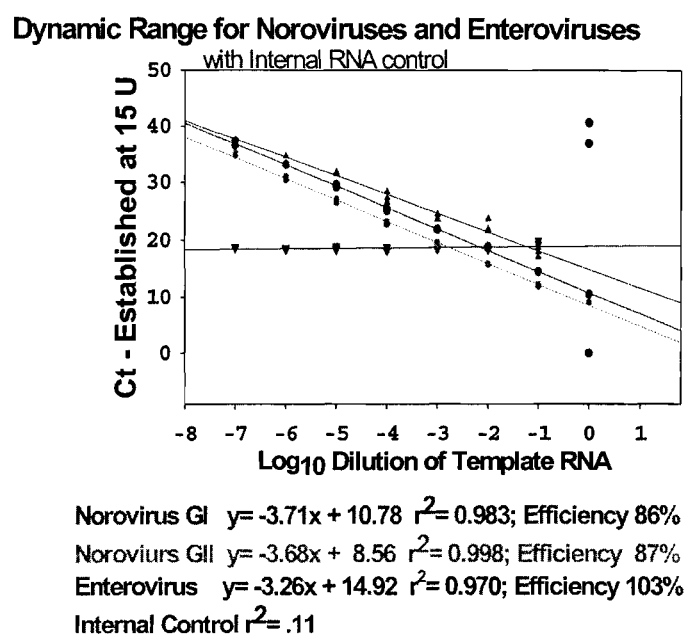
FIG. 6 is determination of the dynamic range for Noroviruses and Enteroviruses. Norovirus Genogroup I, y=−3.71x+10.78, $r^2$=0.983, efficiency=86%; Norovirus Genogroup II, y=−3.68x+8.56, $r^2$=0.998, efficiency=87%; Enterovirus, y=−3.26x+14.92, $r^2$=0.970, Efficiency=103%; Universal internal RNA Control, $r^2$=0.11

The multiplex qRT-PCR assay incorporated a universal internal control to determine amplification efficiency and data normalization. The universal internal RNA control established a single standard curve for all subsequent assays for the detection and/or quantification of each of the target sequences (FIG. 6). The standard curve was dependent upon established Ct values of the universal internal RNA control within the sample and negative template reaction. Ct values of universal internal RNA control intra-and extra-assays were less than 0.5 cycles (approx. 0.1 log). The universal internal RNA control incorporated into each reaction determined whether the conditions within the reaction were optimal (i.e., cycling conditions, primer/probe concentrations, etc.). The universal internal RNA control also determined if and to what extent inhibitory materials or excessive target templates were present in the sample.

Reliable, reproducible standard curves for each of these three virus groups were established ($r^2 > 0.97$) using this real-time, multiplex qRT-PCR assay. Established standard curves were used to quantify target levels. The standard curves were based upon the end-point dilutions and established the end-point as 1 RT-PCR unit. The end-point was established whereby only <2 of 3 reactions gave way to a positive reaction (crossing the Ct) (FIG. 6). Thereby, at least 2 of the 3 reactions for a single sample were within 1 Ct of the internal control.

Example 2

Quantitative Multiplex RT-PCR Assay for the Detection of Noroviruses and Enteroviruses RNA template was serially diluted 1:10 until a dilution of $10^{-9}$. Using the different concentrations of RNA template tested the effect of template overload and the assay's threshold of detectable levels of RNA.

Methods

The cDNAs from the RT-PCR of Example I were purified using a NucleoSpin® Extraction Kit (BD Biosciences Clontech, Palo Alto, Calif.) and cloned using a TOPO TA Cloning® Kit (Invitrogen Corp., Carlsbad, Calif.) by known methods. Clones with full-length inserts and proper orientation were subjected to a QIAprep® Miniprep Kit (Qiagen) to purify their plasmids. Plasmids were purified and sequenced in both the forward and reverse direction to determine and/or verify their sequences. Each plasmid was linearized by restriction digest with BamHI (New England BioLabs®, Inc., Beverly, Mass.) and run on a 1% agarose gel to confirm linearization. The linearized plasmid was subjected to in vitro RNA transcription (MEGAscript® High Yield Kit, Ambion, Inc.). The in vitro reaction components were treated with DNAse. RNA was purified using a MEGAclear™ Kit (Ambion).

The purified RNA was used as template for the multiplex qRT-PCR described in Example 1. The template RNA was serially diluted 1:10 ranging from 0 to $10^{-8}$. Each dilution was used as template RNA for the multiplex qRT-PCR. The resultant PCR product was visualized by 4% TAE gel electrophoresis.

Results and Discussion

Purified RNA from enterovirus, Norovirus GI, and Norovirus GII was serially diluted and reverse transcribed by the multiplex qRT-PCR according to the methods of Example 1. Results were visualized in the graph of FIG. 4 and on a 4% TAE agarose gel (FIG. 5). The fluorescence reported by the GI and GII Norovirus probes signified amplification in addition to the 84 by and 97 by amplicons of the 4% TAE_gel. Template overload inhibited the RT-PCR of the enterovirus and the universal internal RNA control as reported by the fluorescent probes at the 0 and 1:10 dilution of the RNA template. The inhibition of the universal internal RNA control was confirmed by the lack of an amplicon on the 4% TAE_gel for the 0 dilution. However, an enterovirus amplicon was present on the 4% TAE_gel for the 0 dilution. Most likely, the difference between the fluorescence data and the gel electrophoresis may be due to the poor reporting signal strength of the 5' labeled Cy5™ or the concentration of the Taq polymerase used, which had been optimized by the manufacturer for product formation and not for reactions tested.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as adapted and configured, arranged and configured, constructed and arranged, adapted, constructed, manufactured and arranged, and the like.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

What is claimed is:

1. A reverse transcription polymerase chain reaction (RT-PCR) mixture comprising:
   a) an oligonucleotide probe and primers specific for Norovirus Genogroup I;
   b) an oligonucleotide probe and primers specific for Norovirus Genogroup II;
   c) a universal internal nucleic acid molecule, wherein said molecule contains at least one forward primer annealing site, at least one reverse primer annealing site, and at least one amplifiable region;
   d) a universal internal control oligonucleotide probe; and
   e) a universal internal RNA control primer,
   wherein i) the universal internal control oligonucleotide probe comprises SEQ ID NO:13; or
   ii) the universal internal RNA control primer is selected from the group consisting of SEQ ID NO:11, SEQ ID NO:12 and combination thereof; or
   iii) both (i) and (ii).

2. The RT-PCR mixture of claim 1, wherein said oligonucleotide probe of a), b), or d) includes a detectable label.

3. The RT-PCR mixture of claim 1, wherein the primers specific for Norovirus Genogroup I comprise SEQ ID NO: 1 and SEQ ID NO:2.

4. The RT-PCR mixture of claim 1, wherein the primers specific for Norovirus Genogroup II comprise SEQ ID NO: 5 and SEQ ID NO:6.

5. The RT-PCR mixture of claim 1, wherein the oligonucleotide probe specific for Norovirus Genogroup I comprises SEQ ID NO: 3 or SEQ ID NO:4.

6. The RT-PCR mixture of claim 1, wherein the oligonucleotide probe specific for Norovirus Genogroup II comprises SEQ ID NO:7.

7. The RT-PCR mixture of claim 1, wherein the RT-PCR mixture further comprises primers and oligonucleotide probes specific for detection of a RNA virus.

8. The RT-PCR mixture of claim 7, wherein the RNA virus comprises rotavirus.

9. The RT-PCR mixture of claim 7, wherein the RNA virus comprises a positive strand RNA virus.

10. The RT-PCR mixture of claim 9, wherein the positive strand RNA virus comprises Hepatitis A virus or an Enterovirus group virus.

11. The RT-PCR mixture of claim 10, wherein the Enterovirus group comprises poliovirus, coxsackievirus, echovirus, or enterovirus.

12. The RT-PCR mixture of claim 11, wherein the coxsackievirus comprises coxsackievirus Group A or coxsackievirus Group B.

13. A RT-PCR kit comprising the RT-PCR mixture of claim 1 in a package.

14. The kit of claim 13, wherein the kit further comprises instructions for use.

15. A method of reverse transcription-polymerase chain reaction (RT-PCR) comprising:
   a) amplifying a reverse transcribed cDNA in the reverse transcription polymerase chain reaction (RT-PCR) mixture of claim 1;
   b) quantifying Norovirus Genogroup I and Norovirus Genogroup II virus; and
   c) normalizing data to amplification of the universal internal RNA control in the RT-PCR mixture.

16. The method of RT-PCR of claim 15, wherein the primers specific for Norovirus Genogroup I comprise SEQ ID NO: 1 and SEQ ID NO:2.

17. The method of RT-PCR of claim 15, wherein the primers specific for Norovirus Genogroup II comprise SEQ ID NO: 5 and SEQ ID NO:6.

18. The method of RT-PCR of claim 15, wherein the oligonucleotide probe specific for Norovirus Genogroup I comprise SEQ ID NO: 3 and SEQ ID NO:4.

19. The method of RT-PCR of claim 15, wherein the oligonucleotide probe specific for Norovirus Genogroup II comprises SEQ ID NO:7.

20. The method of RT-PCR of claim 1, wherein the universal internal RNA control primer comprises SEQ ID NO:11 or SEQ ID NO:12.

21. The method of RT-PCR of claim 15, wherein the RT-PCR reaction mixture further comprises an oligonucleotide probe and primers specific for a RNA virus.

22. The method of RT-PCR of claim 21, wherein the RNA virus comprises rotavirus.

23. The method of RT-PCR of claim 21, wherein the RNA virus comprises a positive strand RNA virus.

24. The method of RT-PCR of claim 23, wherein the positive strand RNA virus comprises Hepatitis A virus or an Enterovirus group virus.

25. The method of RT-PCR of claim 24, wherein the Enterovirus group virus comprises poliovirus, coxsackievirus, echovirus, or enterovirus.

26. The method of RT-PCR of claim 25, wherein the coxsackievirus is coxsackievirus Group A or coxsackievirus Group B.

27. The method of RT-PCR of claim 15, wherein said cDNA comprises reverse transcribed from RNA in a biological sample.

28. The method of RT-PCR of claim 27, wherein said biological sample comprises blood, urine, or a stool sample.

29. The method of RT-PCR of claim 15, wherein said cDNA comprises reverse transcribed from RNA in a food sample.

30. The method of RT-PCR of claim 29, wherein said food sample comprises shellfish.

31. The method of RT-PCR of claim 15, wherein said cDNA is reverse transcribed from RNA in a water sample.

32. The method of RT-PCR of claim 31, wherein said water sample comprises wastewater, ocean water, lake water, river water, groundwater, or recreational water.

* * * * *